United States Patent [19]
Friddle et al.

[11] Patent Number: 4,738,252
[45] Date of Patent: Apr. 19, 1988

[54] MECHANICAL JOINT CONSTRUCTION

[75] Inventors: Frank E. Friddle, Honea Path, S.C.; Dennis E. Clark, Waterloo, Iowa

[73] Assignee: Friddle's Orthopedic Appliances, Inc., Honea Path, S.C.

[21] Appl. No.: 98,416

[22] Filed: Sep. 18, 1987

[51] Int. Cl.[4] .............................................. F16D 1/12
[52] U.S. Cl. .................................. 128/80 H; 403/97; 128/80 C
[58] Field of Search .................... 403/92, 93, 96, 97; 623/47; 128/89 R, 83.5, 87 R, 80 E, 80 A, 80 F, 80 C, 80 H, 80 J

[56] References Cited

U.S. PATENT DOCUMENTS

| | | | |
|---|---|---|---|
| 3,732,861 | 5/1973 | Lehneis | 128/80 F |
| 3,779,654 | 12/1973 | Horne | 128/80 H |
| 4,102,337 | 7/1978 | Golia | 128/80 E |
| 4,289,122 | 9/1981 | Mason | 128/89 R |
| 4,337,764 | 7/1982 | Lerman | 128/80 F |
| 4,614,181 | 9/1986 | Karlsson | 128/80 F |
| 4,620,532 | 11/1986 | Houswerth | 128/80 C |
| 4,665,904 | 5/1987 | Lerman | 128/80 H |
| 4,666,327 | 5/1987 | Su | 403/96 |

OTHER PUBLICATIONS

Pages I-5, I-6, I-7, and I-8, and D-7, D-8, D-13, and D-14 from an Advertising Catalog of Becker Orthopedic Appliances Co. of Troy, Michigan.
Pages JJ-10, JJ-11, JJ-12, and JJ-13 from an Advertising Catalog Understood to be of Pope Brace Company.

Primary Examiner—Richard J. Apley
Assistant Examiner—James Prizant
Attorney, Agent, or Firm—Luke J. Wilburn, Jr.

[57] ABSTRACT

An improved mechanical joint construction for pivotally interconnecting two members, particularly members of an orthopedic or orthotic body appliance, to limit the degree of pivotal movement between the members and adjustably control the position of limited pivotal movement of the two members; comprising first securement components for attachment to a first appliance member to be interconnected and presenting a generally flat planar surface with pivot pin extending outwardly from the surface and a protrusion on the surface spaced radially from the pivot pin; second securement components for rigid attachment to a second appliance member to be interconnected and comprising an inner peripherally serrated plate with central opening for receipt of the pivot pin to support the inner plate for rotation thereon, an arcuate slot in the inner plate spaced radially from the opening therein and receiving the protrusion for movement between ends of the slot to limit relative rotational movement of the inner plate on the pivot pin, and an outer member having a portion for attachment to the second appliance member to be interconnected and a serrated opening therein for surrounding intermeshing engagement with the peripheral serrations on the inner plate to fix the outer member against relative rotation with respect to the inner plate, and a removable cover plate for securing the inner plate and outer member in adjustable intermeshed engagement on the pivot pin to rotate within limits defined by movement of the protrusion in the inner plate slot.

9 Claims, 3 Drawing Sheets

MECHANICAL JOINT CONSTRUCTION

This invention relates to an improved mechanical joint construction for pivotally interconnecting two members to control pivotal movement of the two members, and, more particularly, to such an improved mechanical joint construction particularly suited for interconnecting two members of a medical orthopedic or orthotic body appliance to control the degree and position of pivotal movement of two appliance members and the corresponding parts of the human body to which the members are attached.

BACKGROUND OF THE INVENTION

Orthopedic, orthotic, and prosthetic devices are widely known and employed for attachment to the human body to replace, adjust, or control of movement of various parts of the body. In orthopedic and orthotic appliances designed for attachment to the foot, leg, arm, or hand of the body, a mechanical joint is often employed to pivotally interconnect two members of the appliance to permit and control relative movement of the members and the corresponding parts of the body to which the members are attached. Orthotic appliances generally are composed of members formed of molded rigid plastic, or other material, which are conformed to fit the shape of the body portion to which they are attached.

In one particular appliance, an ankle foot orthosis, a first molded plastic member of the orthosis shaped to conform to the lower ankle and plantar region of the foot is pivotally interconnected to a second molded plastic member shaped to conform to the rear lower leg and calf of the wearer. The two members are interconnected pivotally at their sides adjacent the ankle of the wearer by mechanical joints to provide lateral support to the lower leg, ankle, and foot of human patients who present weak ankle dorsiflexors coupled with swing and stance phase lateral instability of the subtalar joint. The orthosis permits pivotal movement of the foot about the ankle relative to the lower leg during plantarflexion and dorsiflexion of the foot.

One such prior art ankle foot orthosis connecting joint consists of a pair of pivotally interconnected metal disks for respective attachment to leg and foot members of the orthosis. One of the disks is provided with an arcuate slot radially spaced from the pivot point of the disk. A protrusion on the other disk extends into the slot and moves therealong to limit the relative rotation between the disks and the relative pivotal movement of the two members of the orthosis. The orthosis correspondingly limits dorsiflexion and plantarflexion of the foot relative to the lower leg of the wearer.

Connecting joints for orthosis members also have been comprised of a peripherally serrated circular disk which is fixed to one member, and an arm member attached to a second member. The arm member has a serrated opening therein for receipt of the serrated periphery of the disk to intermeshingly fix the angular position of the arm member relative to the disk. Such joint connectors are thus angularly adjustable, but are not known to provide limited pivotal movement of the members to which they are attached.

Ankle foot orthoses have also been constructed with interconnecting joints consisting of a leg bar secured to a leg-supporting member of the orthosis and pivotally attached to a foot plate secured to a foot-supporting member of the orthosis. The leg bar is further provided with a pair of adjusting screws spaced from and located on either side of the pivot point which engage spaced edge portions of the foot plate which also are radially spaced from its pivotal attachment to the leg bar. Adjustment of either or both of the screws varies and limits the degree of pivotal movement of leg and foot members of the orthosis. Such devices are known as double-action orthoses manufactured by U. S. Manufacturing Company and Becker Orthopedic Appliance Company.

OBJECTS OF THE PRESENT INVENTION

It is an object of the present invention to provide an improved mechanical joint construction for interconnecting two members for limited relative pivotal movement which may be adjustably located through a range of 360°.

It is another object of the present invention to provide an improved mechanical joint construction particulary suited for pivotally interconnecting two members of an orthopedic or orthotic body appliance which functions to both limit the degree of pivotal movement of the two members relative to each other, and to permit arcuate adjustable positioning of the limited pivotal movement through a 360° range.

It is another object of the present invention to provide an improved mechanical joint construction for pivotally interconnecting two members of an orthopedic or orthotic body appliance which is of relatively simple, reliable, and economical construction, and which may be employed to control the extent and location of pivotal movement of the two members and corresponding parts of the human body to which the members may be attached.

BRIEF DESCRIPTION OF THE DRAWINGS

The above, as well as other objects of the present invention will become more apparent, and the invention will be better understood, from the following drawings, when taken with the detailed description thereof, in which.

DETAILED DESCRIPTION OF PREFERRED EMBODIMENTS

Figure 1:
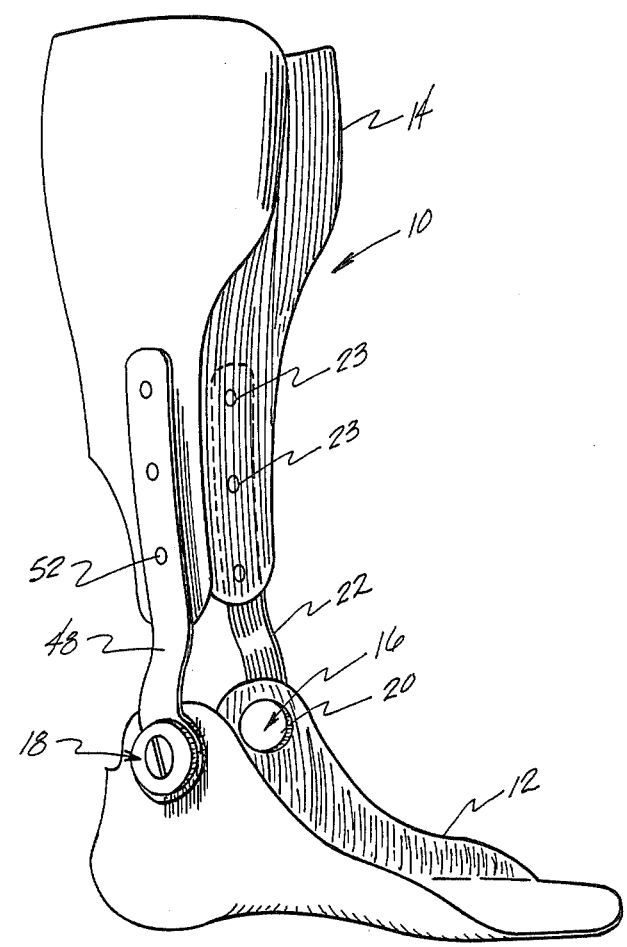
FIG. 1 is a perspective view of an ankle foot orthosis which employs the improved mechanical joint construction of the present invention therein.

The present invention is directed to an improved mechanical joint construction particularly suited for pivotally interconnecting two members of an orthopedic or orthotic appliance to limit the degree of pivotal movement and the position of limited pivotal movement of the two members and corresponding parts of the human body to which the members may be attached. As best seen in FIG. 1, the joint construction of the present invention is illustrated in use in an ankle foot orthosis 10 having a foot-engaging member 12 pivotally interconnected to a calf-engaging leg member 14 by two pivotal joints 16, 18 located on opposite sides of the orthosis to reside adjacent the inside and outside of a wearer's ankle during use. Members 12 and 14 are formed of suitable light-weight rigid material, such as plastic, and are molded or shaped to conform to the shape and size of the body part of the wearer which they engage. The members may be secured to the body of the wearer by conventional straps or bands, not shown.

The pivotal joint 16 may consist of a conventional pivot joint having a base plate 20 attached to the foot-engaging member 12 and pivotally connected to an attachment arm 22 which is correspondingly suitably attached to the leg member 14 of the orthosis by bolts or rivets 23. Joint 16 thus interconnects the orthoses members 12, 14 on one side of the ankle for free pivotal movement during dorsiflexion and plantarflexion of the foot of the wearer. Joint connector 18, which is the improved mechanical joint construction of the present invention, is employed on the other side of the ankle portion of the orthosis 10 to limit pivotal movement of the two members 12 within a specified limit, as will be explained and described.

Figure 2:
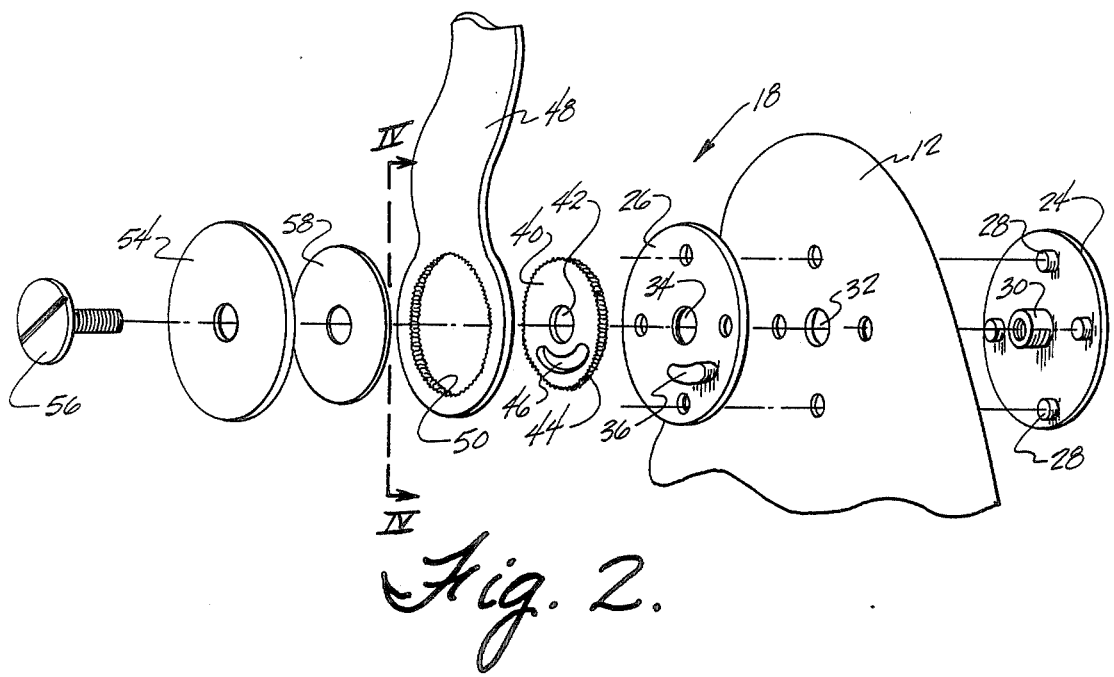
FIG. 2 is an enlarged, perspective view of a portion of the foot-engaging member of the orthosis of FIG. 1, showing, in exploded presentation, the component parts of the improved mechanical joint of the present invention.
Figure 4:
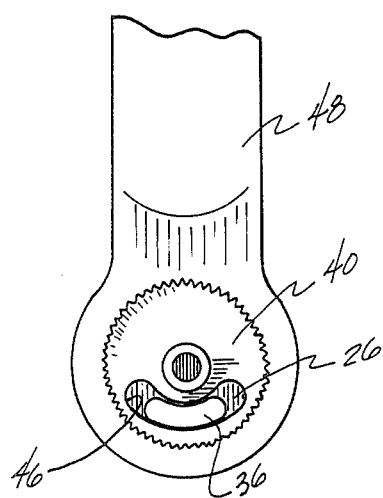
FIG. 4 is side elevation view of three component parts of the assembled joint construction of the present invention as seen in FIGS. 1 and 2, and looking in the direction of arrows IV—IV in FIG. 2.

Mechanical joint construction 18 may best be described in its construction and operation by reference to FIGS. 2 and 4 which show, on an enlarged scale, the component parts of the joint construction. As seen in FIG. 2, joint construction 18 of the present invention comprises first securement means consisting of a metal primary base plate 24 and a metal secondary base plate 26. The base plates are secured to opposite surfaces of foot-engaging member 12 of the orthosis of FIG. 1 in rigid fixed relation by means of suitable elements, such as rivets or studs 28, which extend through corresponding openings in the foot member 12 and secure the primary and secondary base plates to each other. Attached to primary base plate 24 and extending perpendicuarly outward from a central flat peripheral surface thereof are pivot pin means consisting of an internally threaded stub pin 30 which passes through an opening 32 in the orthosis foot member 12 and a central opening 34 in the secondary base plate 26.

Secondary base plate 26 is of generally circular configuration and has a generally flat planer surface from which extends a slightly elongated arcuate protrusion 36 which is spaced radially from central opening 34 and internally threaded stub pin 30 which extends through the central opening of the secondary base plate. Stub pin 30 is of sufficient length to protrude beyond the flat surface of secondary base plate 26 and support a second securement means of the joint construction which is provided for rigid attachment to orthosis member 14, as shown in FIG. 1.

As best seen in FIGS. 2 and 4, the second securement means comprises an inner plate member in the form of a circular disk 40 having a central opening 42 or receipt of the internally threaded stub pin 30 to be supported for rotation thereon. Circular disk 40 has a serrated periphery 44 and is provided with an arcuate slot 46 of greater arcuate length than the arcuate length of protrusion 36. Slot 46 receives protrusion 36 on the secondary base plate for movement therealong to limit the degree of rotation of the circular disk relative to secondary base plate 26.

The second securement means further includes a second outer member comprising an attachment arm 48 having an enlarged end portion with serrated opening 50 therethrough. Opening 50 is sized to surround and intermeshingly engage the serrated periphery 44 of circular disk 40 such that the circular disk and the attachment arm are fixed against relative rotation with respect to each other. As best seen in FIG. 1, attachment arm 44 is suitably fixed to a side portion of the leg member of the orthosis, as by nut and bolt or rivets 52.

As seen in FIG. 2. the second securement means comprising circular disk 40 and attachment arm 48 are secured on the internally threaded stub pin 30 in intermeshed engagement for rotational movement thereabout by means of a cover plate 54 and a fastening bolt 56 which extends through a central opening in plate 54 to be threadably secured within the internally threaded opening of stub pin 30. One or more suitably configured plastic washers, one shown at 58, may be provided stub pin 30 to facilitate rotational movement of the second securement means component parts relative to the cover plate and fastening bolt and first securement means.

FIG. 4 shows, in side elevation view, the operative interrelationship of circular disk 40 and attachment arm 48 of the second securement means, and protrusion 36 of the secondary base plate 26 which resides within the arcuate slot 46 of the circular disk. In assembled relation, the mechanical joint construction of the present invention effectively permits rotational and pivotal movement of the interconnected members 12, 14 of orthosis 10 of FIG. 1 within the limits of movement of the protrusion 36 along as defined by the length of arcuate slot 46 in disk 40. The degree of limited rotational and pivotal movement of the joint construction may be varied to meet the requirements of a particular patient/user by varying the length of the arcuate slot 46 in circular disk 40, and circular disks having arcuate slots of different lengths may be provided for this purpose.

The position of the limited pivotal movement of the two members 12, 14 of the orthosis 10 may be changed or relocated within a full 360° range of movement by removing fastening bolt 56 and cover plate 54. Attachment arm 48 is then removed from intermeshing engagement with the serrated periphery of circular disk 40 and angularly repositioned in intermeshing relationship with the disk at another location and desired angle to the position of the arcuate slot 46.

Figure 3:
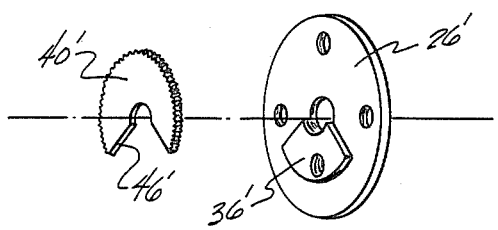
FIG. 3 is a modification of a portion of the joint construction of FIGS. 1 and 2, wherein two of the component parts of the same have been modified in their construction.

FIG. 3 shows a modified form of a joint construction of the present invention wherein the shape of the protrusion on the secondary base plate 26, and the arcuate slot in the circular disk 40 of the joint construction, as seen in FIG. 2, are changed. As seen in FIG. 3, disk 40' forms a partial circle, with an angularly spaced segment thereof removed to form an arcuate slot or opening 46' for receipt of a corresponding protrusion 36' on the secondary base plate. Protrusion 36' on the modified form of the device, as seen in FIG. 3 is free to move within the limits of the sides of the slot 46' in disk 40' to limit pivotal movement in the manner as described with respect to the preferred embodiment of FIGS. 2 and 4.

It can be seen that the mechanical joint construction of the present invention is of relatively compact and economical design, and can be employed to effectively control both the limit of pivotal movement of interconnected parts of an orthopedic or orthotic device or appliance and to permit adjustable positioning of the limited rotational or pivotal movement about a full 360° circle or range.

Although the mechanical joint construction of the present invention has been described and shown in use in interconnection of the lower leg and foot-engaging members of an ankle foot orthosis, it can be appreciated that the joint construction may be employed in other mechanical devices wherein limited pivotal movement of two members with positional adjustable location of such movement about a 360° circle may be desired. As examples, the joint construction may be used in other orthopedic or orthotic appliances employed to control movement of wrist, elbow, knee, or hip joints of the human body, with equal facility of use in such orthopedic braces, orthoses, prostheses, and the like.

That which is claimed, is:

1. An improved mechanical joint construction for pivotally interconnecting two members of an orthopaedic or orthotic device to limit the degree of pivotal movement and to adjustably control the position of limited pivotal movement of the two members, said joint construction comprising:

(a) first securement means for rigid attachment to a first member to be interconnected, said first securement means having a generally flat planer surface, pivot pin means extending perpendicularly out from said surface, and a protrusion fixed to and extending out from said surface and being spaced radially on said surface from said pivot pin means;

(b) second securement means for rigid attachment to a second member to be interconnected, said second securement means including an inner plate member having a serrated outer periphery and a opening therethrough for receipt of said pivot pin means to support said inner plate member for rotation thereon, an arcuate slot in said inner plate member spaced radially from said opening therein and receiving said protrusion for movement therein between ends of said slot to limit relative rotational movement of said inner plate member on said pivot pin means and with respect to said first securement means, said second securement means further including an outer member having a portion for attachment to the second member to be interconnected, said outer member having a serrated opening therein for surrounding the serrated periphery of the inner plate member with the serrations of the plate member and outer member intermeshed to fix the outer member against relative rotation with respect to the inner plate member; and (c) means for securing said inner plate member and outer member in intermeshed engagement on said pivot pin means to permit their limited rotational movement thereon within the limits defined by movement of said protrusion in said slot, and said outer member being arcuately adjustably positionable about the serrated inner plate member upon removal of said securing means to angularly reposition the location of limited rotational movement between said first and second securement means and the members to which they may be attached for interconnection.

2. An improved mechanical joint construction as defined in claim 1 wherein said first securement means comprises a primary and a secondary base plate for attachment to opposite surfaces of a first member to be interconnected for securement in fixed relation thereon, and said secondary base plate defines said relatively smooth planer surface with said protrusion thereon.

3. An improved mechanical joint construction as defined in claim 1 wherein said inner plate member of said second securement means inner plate member comprises a generally circular, peripherally serrated disk having said opening located centrally therein and said arcuate slot in the disk is radially spaced from the central opening and from the periphery of the disk, and said outer member includes an attachment arm extending radially outwardly of the central axis of the serrated opening of the outer member for attachment to a second member to be interconnected.

4. An improved mechanical joint construction as defined in claim 3 wherein said arcuate slot of said circular disk has arcuately shaped end portions, and said protrusion has arcuately shaped shoulder portions which engage the arcuately shaped end portions of the slot at the limits of movement of the protrusion therein to limit relative rotational movement between said attachment arm and said first securement means.

5. An improved mechanical joint construction as defined in claim 1 wherein said inner plate member of said second securement means comprises a disk of partially circular configuration having a serrated outer circular periphery, and said arcuate slot comprises an arcuate segmented opening into the periphery of the disk for receipt of said protrusion for movement therein between the arcuately spaced side edges of the opening.

6. An improved mechanical joint construction as defined in claim 1 wherein said pivot pin means comprises an internally threaded stub pin extending from said first securement means surface, and said securing means for said inner plate member and outer member on said stub pin comprises a cover plate for securement of said inner plate member and said outer member on the stub pin, and fastening bolt means for threaded engagement with said internally threaded stub pin to secure said cover thereon.

7. An improved mechanical joint construction as defined in claim 1 wherein said first and second securement means include means for rigid attachment to respective first and second members of an orthopedic or orthotic appliance to be attached to the human body to limit the degree of pivotal movement and adjustably control the position of limited pivotal movement of respective parts of the human body to which they are attached.

8. An improved mechanical joint construction as defined in claim 7 wherein said first securement means comprises a primary and secondary base plate for attachment to opposite surfaces of a first member of an orthopedic or orthotic appliance for securement in fixed relation thereon, and said second securement means includes an arm member for attachment to a second member of an orthopedic or orthotic appliance in fixed relation thereon.

9. An improved mechanical joint construction as defined in claim 8 wherein said primary and secondary base plates include means for attachment to opposite surfaces of a foot-engaging member of an orthopedic or orthotic device, and said arm member has a portion thereof for attachment to the lower leg-engaging member of an orthopedic or orthotic device.

* * * * *